US011482321B2

(12) United States Patent
Easterhaus et al.

(10) Patent No.: US 11,482,321 B2
(45) Date of Patent: Oct. 25, 2022

(54) PATIENT PORTAL MANAGEMENT OF REFERRAL ORDERS

(71) Applicant: CERNER INNOVATION, INC., Kansas City, KS (US)

(72) Inventors: Kim Michele Easterhaus, Kansas City, MO (US); Daniel Martin Feimster, Shawnee, KS (US); Seth Michel Claybrook, Lee's Summit, MO (US)

(73) Assignee: CERNER INNOVATION, INC., North Kansas City, MO (US)

( * ) Notice: Subject to any disclaimer, the term of this patent is extended or adjusted under 35 U.S.C. 154(b) by 0 days.

(21) Appl. No.: 15/856,449

(22) Filed: Dec. 28, 2017

(65) Prior Publication Data
US 2018/0137590 A1    May 17, 2018

Related U.S. Application Data

(63) Continuation of application No. 13/452,397, filed on Apr. 20, 2012, now abandoned.

(51) Int. Cl.
*G16H 40/20* (2018.01)
*G16H 10/60* (2018.01)
(Continued)

(52) U.S. Cl.
CPC ............. *G16H 40/20* (2018.01); *G06Q 10/10* (2013.01); *G06Q 40/08* (2013.01); *G16H 10/60* (2018.01)

(58) Field of Classification Search
CPC ........ G06Q 50/22; G06Q 10/06; G06Q 10/10; G16H 40/20; G16H 80/00; G16H 10/60; G16H 50/30
(Continued)

(56) References Cited

U.S. PATENT DOCUMENTS 7,363,240 B1    4/2008  Armentano et al.
7,693,727 B2    4/2010  Moore
(Continued)

FOREIGN PATENT DOCUMENTS

WO    WO-2012060899 A2 *  5/2012  ............. G06Q 10/10

OTHER PUBLICATIONS

Weiner, Michael. A Web-based Generalist-Specialist System to Improve Scheduling of Outpatient Specialty Consultations in an Academic Center; Journal of General Internal Medicine 24.6: 710-5. Springer Nature B.V. (Jun. 2009) (Year: 2009).*

*Primary Examiner* — Hiep V Nguyen
(74) *Attorney, Agent, or Firm* — Shook, Hardy & Bacon L.L.P.

(57) ABSTRACT

Methods, computer systems, and computer-readable storage media are provided for creating a patient-centric referral order interface for helping patients manage referral orders via a patient portal. The referral orders are received from a medical organization and include patient-appropriate information but exclude additional information, such as healthcare provider's note providing a detailed reason for referral and a medical note outlining general information about the patient including at least a past medical history and a social history. An option to search for referral providers is provided within the interface and, in some embodiments, available appointment times are provided when it has been determined that no appointments have been scheduled for the referral order.

20 Claims, 12 Drawing Sheets

(51) Int. Cl.
*G06Q 10/10* (2012.01)
*G06Q 40/08* (2012.01)

(58) Field of Classification Search
USPC .............................................................. 705/3
See application file for complete search history.

(56) References Cited

U.S. PATENT DOCUMENTS

| | | | |
|---|---|---|---|
| 7,702,524 B1* | 4/2010 | Whibbs | G06Q 50/22 |
| | | | 705/2 |
| 8,103,524 B1 | 1/2012 | Rogers et al. | |
| 2002/0069085 A1 | 6/2002 | Engel et al. | |
| 2004/0024616 A1* | 2/2004 | Spector | G16H 70/20 |
| | | | 705/2 |
| 2004/0249676 A1 | 12/2004 | Marshall et al. | |
| 2007/0083403 A1 | 4/2007 | Baldwin et al. | |
| 2008/0010087 A1 | 1/2008 | Daniel et al. | |
| 2009/0177453 A1 | 7/2009 | Kouchi et al. | |
| 2009/0292556 A1 | 11/2009 | Chishti et al. | |
| 2010/0106518 A1* | 4/2010 | Kuo | G16H 40/20 |
| | | | 705/2 |
| 2010/0185465 A1 | 7/2010 | Rana et al. | |
| 2011/0173022 A1 | 7/2011 | Mayer et al. | |
| 2011/0191122 A1* | 8/2011 | Kharraz Tavakol | G06Q 10/10 |
| | | | 705/3 |
| 2011/0225001 A1 | 9/2011 | Shen | |
| 2011/0270650 A1 | 11/2011 | Pavagadhi et al. | |
| 2013/0060576 A1 | 3/2013 | Hamm et al. | |
| 2013/0282391 A1 | 10/2013 | Easterhaus et al. | |

\* cited by examiner

WELCOME: ROBERT SMITH | LOG ON | HELP
REFERRAL MANAGEMENT  DIABETES PROGRAM

JOHN DRISCOL  63 Y MALE  DOB: 11/17/1948  MRN: 000012345  INSUR.: BCBS  PCP: JAY SMITH  LAST VISIT: 01/11/2011 — 412

REFERRAL DETAILS — 416

| ACTIVE | HISTORICAL | | |
|---|---|---|---|
| ! CHEST PAIN  TO: PETERSON, JEN | 417  3:24 PM CREATED | FROM: SCHMIDT, JASON  TO: SMITH, ROBERT | 09/16/2011 8:37 AM — 422 |
| HIGH BLOOD PRESSURE  TO: SMITH, ROBERT | 3:24 PM SCHEDULED | <PRIORITY>  HIGH BLOOD PRESSURE — 419 | SCHEDULED 11/03/2011 9:45 AM |
| ! POSSIBLE CANCER  TO: SMITH, ROBERT | TUESDAY SCHEDULED | MR. DRISCOL HAS BEEN SUFFERING FROM HIGH BLOOD PRESSURE FOR THE PAST FIVE YEARS. I HAVE TRIED HIM ON THE FOLLOWING MEDICATIONS...  DIAGNOSIS: HYPERTENSION | |
| PRE-DIABETES, NUTR...  TO: MCALLISTER, AL | 09/03/2011 CREATED | | |
| PERIDONTAL DEISEASE  TO: PETERSON, JEN | 07/27/2011 DRAFT | MEDICAL NOTES  MR. DRISCOL IS A 63 YEAR-OLD WHITE MALE. HE HAS A LONG HISTORY OF DIABETES THAT IS FAIRLY WELL CONTROLLED. HE LIVES AT HOME WITH HIS WIFE... — 420 | |
| ! BEHAVIORAL ISSU...  TO: LEAVITT, BEN | 07/27/2011 CREATED | | |
| KNEE REPLACEMENT  TO: FORSYTHE, JOHN | 07/27/2011 SCHEDULED | | 421 |

WELCOME: ROBERT SMITH | LOG ON | HELP
REFERRAL MANAGEMENT DIABETES PROGRAM 🔍

RICHARD COLLINS — 512 — 75 Y MALE  DOB: 02/19/1936  MRN: 00088785  INSUR.: MEDICARE  PCP: HECTOR  LAST VISIT: 10/02/2010

RECOMMENDED ACTIONS — 514

| | POST ACUTE HOME CARE CONSULT<br>HOME HEALTH SERVICES<br>--<br>DUE BY 10/11/2011 | POST ACUTE PCP FOLLOW-UP<br>CONGESTIVE HEART FAILURE<br>HECTOR LOPEZ, MD<br>DUE BY 10/14/2011 | POST ACUTE CARDIOLOGY FOLLOW-UP<br>CONGESTIVE HEART FAILURE<br>RAJ SINGH, MD<br>DUE BY 10/17/2011 |

FREQUENTLY REFERRED — 516

| | ANNUAL COLORECTAL SCREENING<br>COLORECTAL SCREENING<br>--<br>CENTRAL GASTRO-INTESTINAL | POST ACUTE PHYSICAL THERAPY<br>REHABILITATION SERVICES<br>MARY BOLIN, DPT<br>NORTH COUNTRY REHAB | DIALYSIS CONSULT<br>RENAL FAILURE<br>--<br>WEST ELM DIALYSIS |

TEMPLATES — 518                                         🔍 SEARCH TEMPLATE — 519

| | NEW REFERRAL | GASTROENTEROLOGY CONSULT<br>ABNORMAL COLONOSCOPY<br>JOSEPH JACOBS, MD<br>NORTHWEST MEDICAL CENTER | POST ACUTE LONG TERM CARE CONSULT<br>LONG TERM CARESERVICES<br>--<br>TOWN PLAZA LTC CENTER |
| | POST ACUTE PHYSICAL THERAPY<br>KNEE PAIN<br>--<br>BARRY RIDGE PHYSICAL THERAPY | | |

[ CREATE ]  [ CANCEL ]

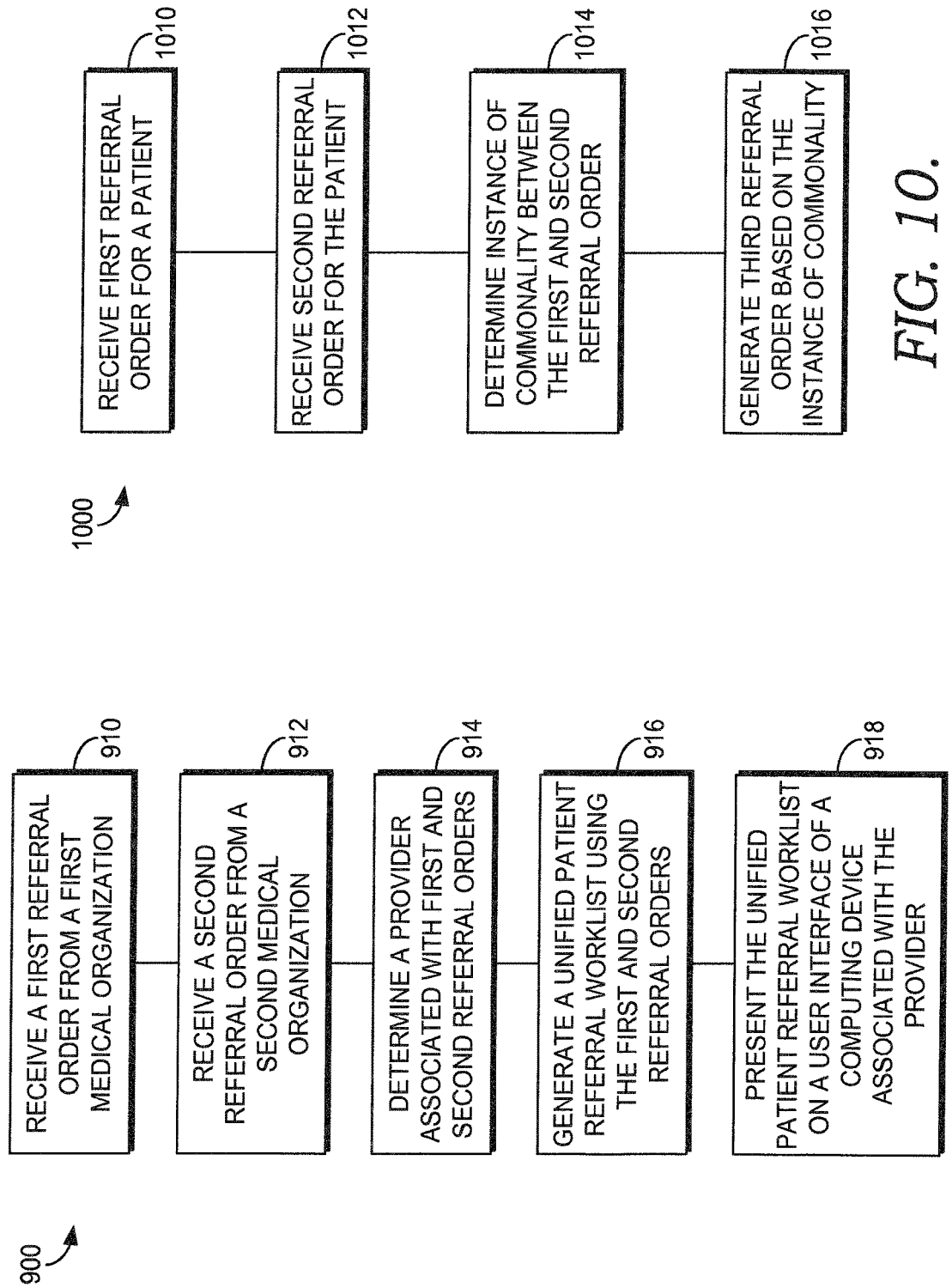

PATIENT PORTAL MANAGEMENT OF REFERRAL ORDERS

CROSS-REFERENCE TO RELATED APPLICATIONS

This application is a continuation of U.S. patent application Ser. No. 13/452,397, entitled "Provider Management of Referral Orders" and filed on Apr. 20, 2012, which is related by subject matter to U.S. patent application Ser. No. 13/452,350 entitled "Patient Management of Referral Orders" and filed on Apr. 20, 2012, both of which are expressly incorporated by reference herein.

BACKGROUND

Patient referrals are a common practice in today's healthcare environment. As healthcare becomes more and more specialized, a provider is less likely to be able to attend to all of his or her patients' needs. In this situation, the patient's provider (the referring provider) will refer the patient to someone (the referral provider) that can address the area of concern. A common practice is for the referring provider to either handwrite a referral order or generate a referral order on the computer and then print the referral order. In both cases, the paper referral order may be given to the patient who hand carries it to the referral provider. In some instances, the referring provider may be able to directly upload the referral order to the referral provider via the Internet, but this requires that the two providers share the same type of electronic medical system.

The referral order often has a bare minimum of information such as the reason for the referral. In fact, the reason for the referral is often a one or two-word sentence such as "hypertension." The referring provider may make the appointment for the patient, or the patient may be responsible for setting up the appointment. Additionally, the patient is often left to look up directions to the referral provider's office. If a patient is scheduled for multiple referrals, there is often no attempt to try and consolidate the referrals at one location. Instead, the patient may have to travel to multiple different locations on different days/times to see the different referral providers. Further, patient preferences regarding such things as gender of the referral provider, board certifications of the referral provider, or ratings of the referral provider are rarely taken into account when generating referral orders. After the patient has seen the referral provider, the referral provider typically sends a letter to the referring provider thanking him or her for the referral and briefly outlining the results of the visit.

There are several drawbacks to the present system. First, the current paper trail of referral orders scattered over multiple patient files makes it difficult for the referring provider to efficaciously and efficiently manage all of her incoming and outgoing referrals. Second, the information that accompanies the referral order is often inadequate. The result is that the referral provider may duplicate tests, questions, and exams that have already been carried out by the referring provider. Additionally, the paucity of information that accompanies a typical referral order may hinder the quality of care administered by the referral provider.

There are also drawbacks to the current referral system from the patient's perspective. For instance, there is currently not an effective way for a patient, or the patient's family, to manage his or her referrals. This can be a problem for patients with multiple medical issues that have multiple referral orders directed to different providers. Referring providers may set up appointment times for the patient without first getting input regarding convenient times or locations. The lack of consolidation in the case of multiple referral orders directed to referral providers at different locations may mean that the patient is traveling unnecessarily in an attempt to visit the different referral providers. Additionally, patients may have important feedback regarding the quality of care received from the referral provider, but this feedback is rarely captured and communicated back to the referring and/or referral provider. This feedback could help to improve the quality of the providers' practices.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

In brief, and at a high level, the present invention is directed to methods, systems, and computer-readable storage media for creating, among other things, a unified patient referral worklist that helps a provider to manage incoming and outgoing referrals. The unified patient referral worklist is generated by aggregating referral orders for patients from different medical organizations and determining which of the referral orders are associated with the provider; the unified patient referral worklist is generated based on this information. The present invention is additionally directed to generating patient-centric referral orders. For example, an instance of commonality, such as location, is found between the different referral orders for a patient, and the patient-centric referral order is generated based on the instance of commonality. The result is that the patient is able to visit one location and have his or her referral order needs met at that one location. The present invention is also directed to generating a plurality of referral order options that enable a provider to select from recommended referral orders, frequently occurring referral orders, and/or customized referral orders.

BRIEF DESCRIPTION OF THE DRAWINGS

Embodiments are described in detail below with reference to the attached drawing figures, wherein:

FIG. 4 depicts an exemplary graphical user interface for presenting a detail view of a referral order in accordance with an embodiment of the present invention;

FIG. 5 depicts an exemplary graphical user interface for presenting a plurality of referral order options in accordance with an embodiment of the present invention;

FIG. 8 depicts an exemplary graphical user interface for presenting a referral management user interface in conjunction with a second application in accordance with an embodiment of the present invention;

FIG. 9 is a flow diagram that illustrates an exemplary method of generating a unified patient referral worklist in accordance with an embodiment of the present invention;

FIG. 10 is a flow diagram that illustrates an exemplary method of generating a patient-centric referral order in accordance with an embodiment of the present invention;

DETAILED DESCRIPTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, computer systems, and computer-readable storage media that help a patient to manage his or her referral orders. Referral orders for the patient are aggregated, and patient-appropriate information is identified and extracted from the referral orders. A set of modified referral orders is generated based upon the patient-appropriate information and is displayed to the patient on a user interface. The patient is able to interact with the user interface. For instance, the patient can view details concerning pending referral orders as well as past referral orders. Available appointment times for referral providers may be provided, and the patient can select a time that works within the patient's schedule. As well, the patient can provide feedback regarding the quality of care received from the referral provider; the feedback may subsequently be communicated to the referring provider and/or the referral provider.

Additionally, embodiments of the present invention are directed to methods, computer systems, and computer-readable storage medium for creating, among other things, a unified patient referral worklist that helps a provider to manage incoming and outgoing referrals. The unified patient referral worklist is generated by aggregating referral orders for patients from different medical organizations and determining which of the referral orders are associated with the provider; the unified patient referral worklist is generated based on this information. The present invention is additionally directed to generating patient-centric referral orders. For example, an instance of commonality, such as location, is found between the different referral orders for a patient, and the patient-centric referral order is generated based on the instance of commonality. The result is that the patient is able to visit one location and have his or her referral order needs met at that one location. The present invention is also directed to generating a plurality of referral order options that enable a provider to select from recommended referral orders, frequently occurring referral orders, and/or customized referral orders.

Figure 1:
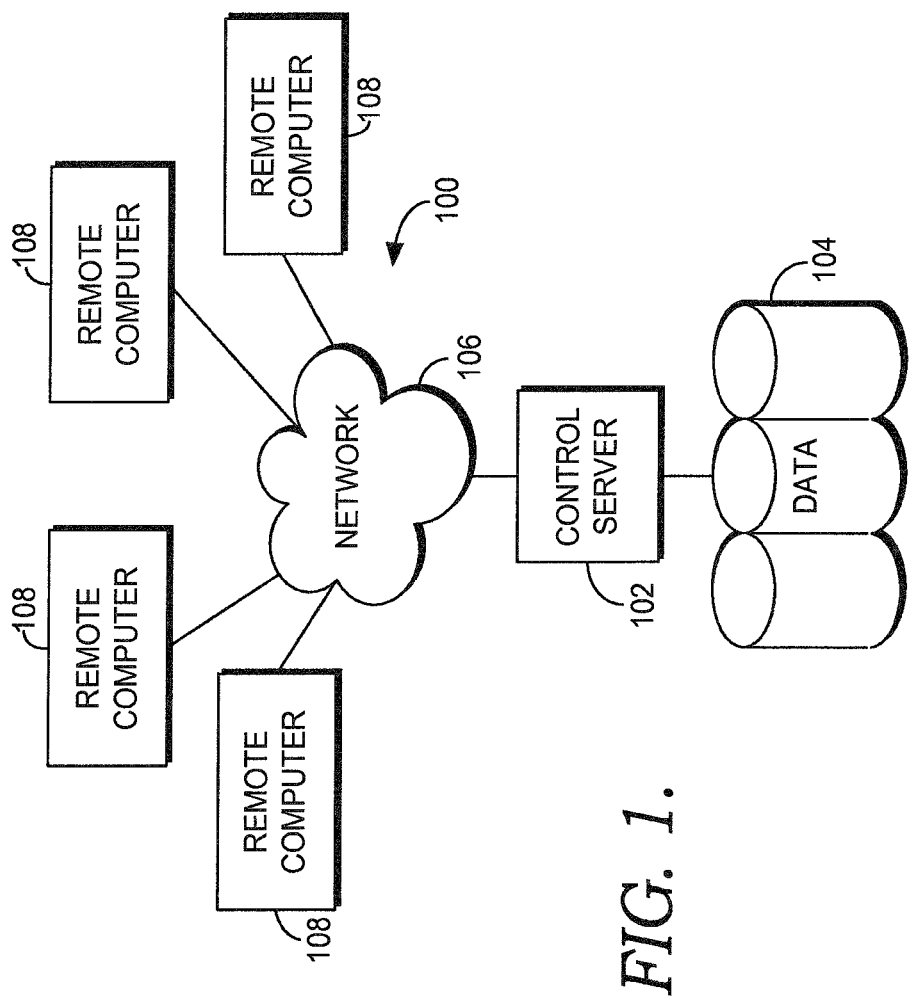
FIG. 1 is a block diagram of an exemplary computing environment suitable to implement embodiments of the present invention.

Having provided a high-level overview of the present invention, an exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and providers' offices. Providers may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. As well, a provider may comprise an organization made up of one or more clinicians. For instance, an outpatient clinic that employs a group of physicians may be considered a provider. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
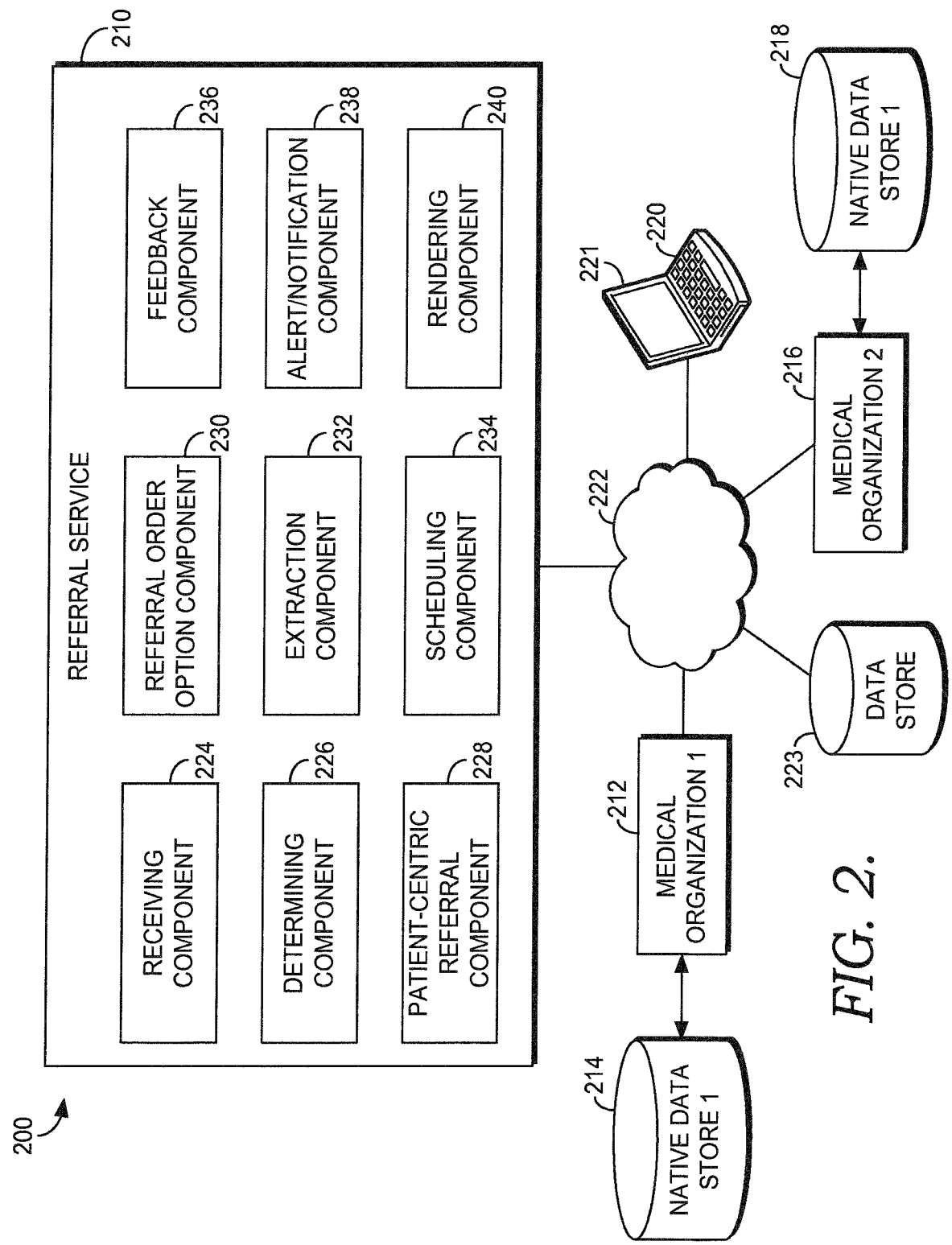
FIG. 2 is a block diagram of an exemplary computing system environment suitable for managing referral orders suitable to implement embodiments of the present invention.

Turning now to FIG. 2, an exemplary computing system environment 200 is depicted. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes a referral service 210, a first medical organization 212 with a first native data store 214, a second medical organization 216 with a second native data store 218, an end-user computing device 220 with a display screen 221, and a data store 223 all in communication with one another via a network 222. The network 222 may include, without limitation, one or more local area networks (LANs) and/or wide area networks (WANs). Such networking environments are commonplace in offices, enterprise-wide computer networks, intranets and the Internet. Accordingly, the network 222 is not further described herein.

In some embodiments, one or more of the illustrated components/modules may be implemented as stand-alone applications. In other embodiments, one or more of the illustrated components/modules may be integrated directly into the operating system of the referral service 210. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the referral service 210 might reside on a server, cluster of servers, or a computing device remote from one or more of the remaining components.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

As shown in FIG. 2, the referral service 210 is capable of communicating with the first medical organization 212 and the second medical organization 216 in order to obtain patient medical information. The medical organizations 212 and 216 may include hospitals, clinics, providers' offices, and the like. Patient information collected from the first medical organization 212 and the second medical organization 216 may include, but is not limited to, information that is stored in association with a patient's electronic medical record (EMR). Information in the EMR describes various aspects of the patient state, including patient vitals, lab results, medication orders, referral orders, diagnosis codes, condition codes, clinical orders, indexed values from clinical notes or other text documents, patient demographic information, patient history, patient images, and a variety of other patient information.

It should be noted that the medical organizations 212 and 216 shown as communicating with the referral service 210 in FIG. 2 are provided by way of example only and are not intended to limit the scope of the present invention in any way. Each medical organization 212 and 216 may have one or more computing devices, such as the computing device 100 of FIG. 1, for communicating with the referral service 210. Each medical organization 212 and 216 may maintain its own enterprise healthcare system, and each organization 212 and 216 may not be directly connected with one another such that separate medical record systems may be utilized by each medical organization 212 and 216. The medical organizations 212 and 216 send information to the referral service 210 but do not typically send information between one another. In addition, communication between the referral service 210 and the medical organizations 212 and 216 may be via one or more networks, which may comprise one or more wide area networks (WANs) and one or more local area networks (LANs), as well as one or more public networks, such as the Internet, and one or more private networks.

Further, the medical organizations 212 and 216 may be able to access the referral service 210 in a variety of ways within the scope of the present invention. For example, in some embodiments, the medical organizations 212 and 216 may have a native clinical computing system, which may be able to communicate with the referral service 210. In other embodiments, a client application associated with the referral service 210 may reside or partially reside on one or more of the medical organization's computing devices facilitating communication with the referral service 210. In further embodiments, communication may simply be a web-based communication, using, for example, a web browser to communicate to the referral service 210 via the Internet. Any and all such variations are contemplated as being within the scope of embodiments of the present invention.

The native data stores 214 and 218 are configured to store information for use by, for example, the medical organizations 212 and 216 and/or the referral service 210. The information stored in association with the native data stores 214 and 218 is configured to be searchable for one or more items of information stored in association therewith. The native data stores 214 and 218 store patient records, such as electronic medical records (EMR) that can be accessed by various applications.

The EMR may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders including past referral orders, completed orders, pending orders including pending referral orders, tasks, lab results, other test results, patient encounters and/or visits, immunizations, physician comments, nurse comments, other caretaker comments, and a host of other relevant clinical information.

As shown, the end-user computing device 220 includes a display screen 221. The display screen 221 is configured to display information to the user of the end-user computing device 220, for instance, information relevant to communications initiated by and/or received by the end-user computing device 220, information concerning referral orders, and/or the like. Embodiments are not intended to be limited to visual display but rather may also include audio presentation, combined audio/visual presentation, and the like. The end-user computing device 220 may be any type of display device suitable for presenting a graphical user interface. Such computing devices may include, without limitation, a computer, such as, for example, any of the remote computers 108 described above with reference to FIG. 1. Other types of display devices may include tablet PCs, PDAs, mobile phones, smart phones, as well as conventional display devices such as televisions.

The data store 223 is configured to store information for use by, for example, the referral service 210. The information stored in association with the data store 223 is configured to be searchable for one or more of the items of information stored in association therewith. The information stored in association with the data store 223 may comprise general information used by the referral service 210. For example, the data store 223 may store information concerning usage patterns of providers. The usage patterns may relate to how often a provider generates a particular referral order. Additionally, the data store 223 may store information concerning decision-support algorithms, reference materials, standards of care, recommendation protocols, and the like. This information may be specific to the healthcare facility to which the provider is associated, or the information may be promulgated by, for example, nationally-recognized medical organizations or governing bodies. This information may be used by the referral service 210 to determine, for example, recommended referrals for a patient.

The content and volume of such information in the data store 223 are not intended to limit the scope of embodiments of the present invention in any way. Further, though illustrated as a single, independent component, the data store 223 may, in fact, be a plurality of storage devices, for instance, a database cluster, portions of which may reside on the referral service 210, the end-user computing device 220, and/or any combination thereof.

Components of the referral service 210 may include a processing unit, internal system memory, and a suitable system bus for coupling various system components, including one or more data stores for storing information (e.g., files and metadata associated therewith). The referral service 210 typically includes, or has access to, a variety of computer-readable media.

The computing system environment 200 is merely exemplary. While the referral service 210 is illustrated as a single unit, it will be appreciated that the referral service 210 is scalable. For example, the referral service 210 may in actuality include a plurality of computing devices in communication with one another. Moreover, the data store 223, or portions thereof, may be included within, for instance, the referral service 210 as a computer-storage medium. The single unit depictions are meant for clarity, not to limit the scope of embodiments in any form.

As shown in FIG. 2, the referral service 210 comprises a receiving component 224, a determining component 226, a patient-centric referral component 228, a referral order option component 230, an extraction component 232, a scheduling component 234, a feedback component 236, an alert/notification component 238, and a rendering component 240. In some embodiments, one or more of the components 224, 226, 228, 230, 232, 234, 236, 238, and 240 may be implemented as stand-alone applications. In other embodiments, one or more of the components 224, 226, 228, 230, 232, 234, 236, 238, and 240 may be integrated directly into the operating system of a computing device such as the remote computer 108 of FIG. 1. It will be understood that the components 224, 226, 228, 230, 232, 234, 236, 238, and 240 illustrated in FIG. 2 are exemplary in nature and in number and should not be construed as limiting. Any number of components may be employed to achieve the desired functionality within the scope of embodiments hereof.

The receiving component 224 is configured to receive patient-related medical information such as referral orders and medical information stored in association with, for example, the native data stores 214 and 218. Additionally, the receiving component 224 is configured to receive user inputs, requests, and/or selections. For the purposes of this application, a user may be defined as a provider, a member of the provider's office, a patient, a member of the patient's family, and/or a healthcare facility involved in the patient's care.

A referral order is a temporary or permanent transfer of care for a patient from a referring provider to a referral provider. Referral orders may be received by the receiving component 224 from one medical organization, such as the first medical organization 212, or referral orders may be received from multiple medical organizations. Further, the different medical organizations may have disparate medical record systems that limit direct interoperability with each other. The referral orders received by the receiving component 224 may concern one patient or multiple patients. Any and all such variations are contemplated as being within the scope of the invention.

The referral orders may include patient identifying information, reason for referral, payment or insurance information, provider information (who is the referring provider and who is the referral provider), appointment times and dates, status of the referral (when the referral order was created, whether the referral order is pending or has already occurred, etc.), priority levels (urgent versus routine), referral notes concerning the reason for the referral, and medical notes outlining general information about the patient including past medical history, social history, and the like. The referral orders may also include attachments such as test results, procedure results, and other types of medical documentation.

The determining component 226 is configured to determine all incoming and outgoing referrals for a specific provider and generate a unified patient referral worklist for the provider that reflects this information. Any one provider may act as both a referring provider and a referral provider. For example, a provider may be a family practice physician trained to treat a wide-variety of common problems. The family practice physician may have a diabetic patient who is in need of a thorough ophthalmologic exam. This is outside the family practitioner's realm of expertise, so the family practice physician refers the patient to an ophthalmologist. In this case, the family practice physician is acting as a referring provider, and the ophthalmologist is the referral provider. The family practice physician can also be a referral provider. Continuing with the example given above, the ophthalmologist may encounter a patient who is looking for a good family practice physician, and the ophthalmologist refers the patient to the family practice physician. Here, the family practice physician is in the role of referral provider, and the ophthalmologist is the referring provider.

The determining component 226 generates the unified patient referral worklist by analyzing received referral orders (e.g., received by the receiving component 224) and determining referral orders that are associated with a particular provider. Referral orders may be associated with a provider if the referral order indicates that the provider is a referring provider or a referral provider. The referral orders associated with the particular provider are aggregated and the uniform patient referral worklist for the provider is generated using this information. Thus, the unified patient referral worklist is a list of all incoming and outgoing referral orders for a provider. The unified patient referral worklist may be rendered by the rendering component 240 on a user interface of a computing device associated with the provider.

Figure 3:
FIG. 3 depicts an exemplary graphical user interface for presenting a unified patient referral worklist in accordance with an embodiment of the present invention.

FIG. 3 depicts an exemplary graphical user interface (GUI) 300 displaying a unified patient referral worklist generated by a determining component such as the determining component 226 of FIG. 2. The GUI 300 includes an area 312 that identifies the provider associated with the worklist. The provider may comprise an individual clinician, a group of clinicians who work together, or an office associated with a clinician(s). The provider may access the worklist after undergoing an authorization and authentication process in order to ensure the privacy and safety of the patient information.

The GUI 300 also includes a unified patient referral worklist 314. The worklist 314 includes a series of selectable rows. Each row is associated with either an incoming or outgoing patient referral. Each row may include, at least, information such as patient identifier, reason for referral, priority (urgent versus routine), appointment time and date, provider information, payment information, and status (pending, created, pending and scheduled, overdue, cancelled, etc.).

The GUI 300 also includes a filtering area 316 that enables a provider or employees in the provider's office to filter the incoming and outgoing referrals. As seen, filtering options may include referrals for review, requested referrals, rejected referrals, outbound referrals, referrals in progress, and/or referrals for assessment. Additionally, the provider or employees in the provider's office may select multiple filtering options to create a custom worklist which can be subsequently saved. For example, a custom worklist may be generated for a provider especially if the provider is a member of a multi-provider group (i.e., "Dr. Bob's Family Practice"). Any and all such variations are contemplated as being within the scope of the invention.

The GUI 300 further includes a sorting area 318. For example, referrals may be ordered based on, for example, gender, type of insurance, referring provider, the date the referral was received and/or created, or ordered alphabetically. The GUI 300 also includes a new referral area 320. Selection of a selectable option associated with the new referral area 320 navigates the user to a number of referral order options. These options will be discussed in greater depth below.

Upon selection of an incoming or outgoing referral such as, for example, referral 321, the provider is navigated to a detail screen comprising detailed information about the referral 321. FIG. 4 illustrates this aspect of the invention. FIG. 4 depicts an exemplary graphical user interface (GUI) 400. The GUI 400 includes a patient identification area 412 that provides information concerning the patient who is the subject of the referral order. The information includes, for example, name, age, sex, weight, height, date of birth, patient number, payment information, primary care provider, date of last visit, and the like. The GUI 400 also includes a selectable active referral tab 414. Selection of the tab 414 displays all incoming and outgoing active referrals associated with the patient; this information is shown in the active referral area 418.

The active referral area 418 enables all the providers who provide care to the patient (e.g., referring providers and referral providers) to view details concerning pending referral orders associated with the patient. The referral orders may be ordered chronologically from newest to oldest or vice versa. For example, in this case, a referral provider (Robert Smith) can view details concerning the incoming referral orders for him, and he can also view details about other referral orders associated with the patient even though those referral orders may involve different referral providers. This gives the referral provider a comprehensive view of the patient's health and may improve the quality of care provided to the patient.

Selection of one of the active referrals, such as referral 417, in the active referral area 418, initiates a display of details associated with the referral 417. The details are displayed in a referral comments section 419 and/or a medical documentation area 420. The referral comments section 419 presents comments pertaining to the referral; the comments may have been inputted by the referring provider. The referral comments section 419 may also include a priority indicator (urgent versus routine), status of the referral (currently pending, cancelled, completed, created, and/or draft), date and time when the appointment is scheduled, and diagnosis. The medical documentation area 420 may present medical notes or documentation to better assist the referral provider; the medical note may have been inputted by the referring provider. The medical note may include information such as past medical history, social factors (e.g., whether the patient's family is involved in the patient's care), demographic factors (e.g., whether the patient smokes, drinks, etc.), and other information that may impact the patient's care. The medical documentation area 420 also includes an attachment area 421 where the referring provider can attach pertinent clinical documentation (lab results, procedure results, patient history, a pre-visit questionnaire completed by the patient, radiographic images, EKGs, etc.) to further assist the referral provider.

The GUI 400 further includes a historical referral tab 416. Selection of the historical referral tab 416 presents all past referrals associated with the patient. The historical referrals are presented similar to the active referrals in the active referral area 418. Selection of one or more of the historical referrals initiates the presentation of details associated with the historical referral order (i.e., referral comments and medical documentation) in the referral comments section 419 and the medical documentation area 420.

The GUI also includes a selectable action tab 422. The referral service 210 of FIG. 2 defines actions based on the status of the referral. For instance, if a referral has already been scheduled, one of the actions may include cancelling the referral. Another action may include marking the referral order as completed. Additionally, when a referral order has been marked as completed, an input field may be presented to the referral provider. The referral provider can input a referral note and attach any pertinent information to the referral note. The referral note is subsequently made available to the referring provider via, for example, email, text, fax, mail, presentation on a user interface, and the like.

Turning back to FIG. 2, the referral service 210 further includes the patient-centric referral component 228. The patient-centric referral component 228 is configured to aggregate pending referrals for a patient and determine at least one instance of commonality between the different referrals. For example, this may be accomplished by determining a medical specialty associated with each of the referral orders and then determining one or more common locations that include providers practicing most or all of the medical specialties. In another example, a provider or team of providers associated with each of the referral orders may be determined, and one or more locations that include the provider or team of providers may then be determined. Other instances of commonality between the different referral orders may include gender of the provider, ratings of the providers, provider affiliations, board certifications, payments accepted, and the like.

The patient-centric referral component 228 may apply one or more user-selected filters to the one or more instances of commonality. Filters may include locations within a predetermined distance of the patient's home, providers that accept certain types of insurance or payment, providers that have received favorable ratings (e.g., quality ratings, healthcare consumer ratings, financial ratings, etc.), locations that have available appointment times, providers of a specific gender or specialty, providers who are board certified, or user-customized filters. The patient-centric referral component 228 may also substantially match or apply other pieces of patient information to the one or more instances of commonality. The other pieces of patient information may include age of the patient, medical history of the patient, the patient's support system (e.g., family support), and the like.

Further, the patient-centric referral component 228 is further configured to generate a patient-centric referral order based on, for example, the one or more instances of commonality, the user-selected filters, and the patient information. By way of illustrative example, an instance of commonality between different referral orders may include one or more common locations. The one or more common locations may further be matched to a geographic location of the patient to determine which of the one or more locations is closest to the patient. A patient-centric referral order would then be generated based on the matched information. In another example, an instance of commonality between different referral orders may include gender of the provider(s). The gender of the provider may be matched to a patient preference regarding the gender of treating providers, and a patient-centric referral order generated based on the matched information. The patient-centric referral order may be rendered on a user interface by the rendering component 240.

As mentioned above, the patient-centric referral component 228 may determine more than one instance of commonality. For instance, the combination of medical specialties may be practiced at more than one location. In one aspect of the invention, the multiple locations are presented to the user (i.e., by the rendering component 240), and the user is able to select a location from among the multiple locations. Any and all such variations are contemplated as being within the scope of the invention.

Figure 7:
FIG. 7 depicts an exemplary graphical user interface for presenting a patient-centric referral order in accordance with an embodiment of the present invention.

Turning to FIG. 7, an exemplary graphic user interface (GUI) 700 is depicted and illustrates the presentation of a patient-centric referral order. The GUI 700 includes a patient identification area 712 that presents similar information as outlined above with respect to the patient identification area 412 of FIG. 4. The GUI 700 also includes a search result area 715 configured to present one or more referral orders. In this example, the search result area 715 includes a patient-centric referral order 714. The patient-centric referral order 714 includes two referrals (Post Acute Cardiology Follow-Up, and Post Acute Primary Care Provider Follow-Up) that involve two different specialties (cardiology and general respectively). A patient-centric referral component, such as the patient centric-referral component 228 of FIG. 2, has identified a common location (Northland Medical Group) that includes the two specialties. The GUI 700 additionally includes a filter area 718 where a user can apply one or more filters to further refine the patient-centric referral order 714 by, for example, distance, type of insurance accepted, ratings, favorites, wait time, and the like. Although the instance of commonality in this case is a common location by medical specialty, it is contemplated that other instances of commonality may be used to generate the patient-centric referral order 714.

The search result area 715 also includes a third referral order 716. The third referral order 716 may be one for which an instance of commonality (e.g., location) with the other two referral orders could not be found. If more than one provider is determined to be associated with the third referral order 716, the different providers may be presented in a suggested provider area 722. The providers in the suggested provider area 722 may be presented in conjunction with ratings (illustrated by the stars) based on, for example, healthcare consumer reviews, reviews by rating services, financial ratings, and the like. The suggested provider area 722 may also include location information, contact information, and available appointment times. The available appointment times may be generated and presented in near real-time utilizing cloud-based scheduling. The provider is able to select an appointment time for the patient (for example, appointment time 723), or the patient may select an appointment time utilizing a patient portal user interface; this will be discussed with respect to FIG. 13. Selection of a provider and/or time in the suggested provider area 722 may be submitted and/or cancelled via the submit/cancel buttons in area 724.

Still further, the GUI 700 includes a search results box 720 that enables a user to search results within the search result area 715. Although only three results are shown in the search results area 715, it is contemplated that a longer list of referral orders could be presented. The user can utilize the search results box 720 to quickly search within the search results. The search could be based on, for example, provider, location, ratings, medical specialty, available appointment times, and the like.

Again turning back to FIG. 2, the referral order option component 230 is configured to determine and generate a plurality of referral order options for a patient. For instance, the referral order option component 230 may determine recommended referral options based on a patient's medical record and medical standards of care; the standards of care may be stored in association with, for example, the data store 223. By way of illustrative example, the patient's medical record may indicate that the patient is 55-years-old and has not had a screening colonoscopy. Medical standards of care recommend that a person of average risk should have a screening colonoscopy every ten years starting at the age of 50. The referral order option component 230 may generate a referral order option directed toward this recommendation.

The recommended referral order options may be pre-populated with information such as reason for referral, patient name, due date, and the like. The recommended referral order options may also be pre-populated with referral provider names. The referral providers may be selected based on contractual obligations set forth the in the patient's medical insurance plan.

The referral order option component 230 may also determine and generate referral order options based on referral orders that are frequently generated by the provider. The provider's referral patterns are analyzed along with a patient's medical record. Based on this information, the referral order option component 230 generates options for the provider. The referral order option component 230 may monitor referral patterns based on, for example, referring provider, referral provider, specialty, reason for referral, location, and the like. By way of example, a referring provider may frequently refer all her patients who have suffered a heart attack to a particular cardiologist for follow-up. When it is determined that the referring provider wishes to generate a referral order for a patient who has suffered a heart attack (determined from the patient's medical record), the referral order option component 230 generates a referral order option directed to the particular cardiologist. The referral order option component 230 is further configured to generate templates that can be used by a provider or a medical facility to generate a customized referral order. The different referral order options (recommended, frequently occurring, and templates) may be rendered on a user interface by the rendering component 240.

FIG. 5 depicts an exemplary graphical user interface (GUI) 500 illustrating the presentation of a plurality of referral order options. The GUI 500 may be initiated upon receiving an indication that the provider wishes to generate a new referral. For example, turning back to FIG. 3, the GUI 300 includes a new referral option 320. Upon selection of the new referral option 320, the user is navigated to, for example, the GUI 500.

The GUI 500 includes a patient identification area 512 that identifies the patient for whom the referral orders are being generated. The patient identification area 512 is similar to the patient identification area 412 of FIG. 4. The GUI 500 also includes a recommended referral order option area 514. As mentioned above, recommended referral order options may be generated by a referral order option component based on the patient's medical history and standards of care. The standards of care may be state or national standards of care, or standards of care particular to the provider's healthcare organization. The recommended referral order options in the area 514 are pre-populated to varying degrees with information such as patient name, reason for referral, provider name, due date, and type of referral.

In another aspect, the recommended referral order options may be based on recommendations unique to the provider. For instance, the provider may like all of his patients to have a baseline chest X-ray at age 40 even though standards of care may not recommend a baseline chest X-ray until age 45. Thus, upon the system determining that a patient has not had a baseline chest X-ray and is 41-years-old, a recommended referral order option directed to a baseline chest X-ray is generated and presented in the recommended referral order option area 514. In still yet another aspect, the recommended referral order options may be based in part on patient preferences gleaned from the patient's medical history. For example, the patient may have seen a cardiologist a short time ago for a problem unrelated to the present problem. If the patient is currently due for a routine EKG, one of the recommended referral order options may include the cardiologist.

The GUI 500 also includes a frequently referred option area 516. As mentioned, options in the frequently referred option area 516 are generated based on the provider's referral patterns and the patient's medical history. The provider's referral patterns may include provider locations frequently referred to, providers frequently referred to, specialties frequently referred to, and frequently occurring reasons for referral. The frequently referred options may be pre-populated with information such as patient name, provider name, location, type of consult, and reason for referral.

Additionally, the GUI 500 includes a customized template area 518. The area 518 may include templates customized by a healthcare organization to which the provider is affiliated as well as blank templates. The customized area 518 also includes a search template box 519 by which the provider can search for templates that have been created but are not displayed.

Figure 6:
FIG. 6 depicts an exemplary graphical user interface for presenting a detail view for a referral order option in accordance with an embodiment of the present invention.

Each of the referral order options shown in the GUI 500 is selectable. Upon selection of one or more referral order options, the user is navigated to a user interface where the user can add details to the selected referral order option. FIG. 6 depicts an exemplary GUI 600 illustrating a detail screen presented upon selection of one or more of the referral order options. The GUI 600 includes a patient identification area 612 similar to those already described. The GUI 600 also includes referrals 614 and 615 that were selected in relation to the GUI 500. Upon selection of, for example, the referral 615 ("Yearly Physical"), input areas are presented. The input areas include a reason for referral area 616 and a medical documentation area 622.

The reason for referral area 616 includes a number of input fields where the provider can input, for example, a reason for referral, a priority, type of referral, a specialty associated with the referral provider, and the like. This information may also be pre-populated by, for example, a referral order option component. The referral area 616 also includes input fields for a referral note 620 where the referring provider can provide specific details pertaining to the reason for referral. As well, there in an attachment area 618 where the provider can attach clinical documentation associated with the patient (clinical notes, history and physical, radiographs, lab results, procedure results, and the like). Any clinical documentation attached in the attachment area 618 can be persisted to other referral orders being created at the same time such as the referral 614.

The medical documentation area 622 has an input field by which the referring provider can write a general note applicable to any number of referrals for the patient. The note may detail general information about the patient including the patient's social history, past medical history, family support, and the like. The note may be persisted to other referral orders being created by the provider for the patient. Once a referral order has been created by the provider, the provider may save the referral order, or cancel the referral order using the selectable buttons associated with area 626. The area 626 also has a save for later option that places the referral order on a pending list so that the provider or another user (e.g., an employee in the provider's office) can finish the referral order at a later point in time. The area 626 further includes a continue button by which the referring provider can search for referral providers.

In another aspect, a referring provider can write a general note applicable to a number of different patients. For example, a nurse who oversees care for diabetic patients may review a list of diabetic patients that have not had a yearly eye exam. The nurse may initiate an eye exam referral order for multiple patients at once. The medical note in this case could be a general note outlining information about the patient being diabetic and in need of an eye exam. Patient specific details could be filled in at a later point in time.

The GUI 600 also has a patient information display area 624 that displays patient information drawn from the patient's EMR. The patient information display area 624 helps the provider to accurately and quickly generate a referral order using up-to-date patient information. For instance, the patient information display area 624 includes a listing of all the patient's problems, medications the patient is taking, allergies, provider recommendations, office visits, documents, health history, past and pending referrals, and the like.

Turning back to FIG. 2, the referral service 210 also includes the extraction component 232. The extraction component 232 is configured to identify and extract patient-appropriate information from one or more referral orders associated with a patient. Patient-appropriate information is information that is relevant to the patient. Such information may include referral provider names and specialties, locations associated with providers, priority information (urgent versus routine), ratings associated with providers, appointment times and dates, reason for referral, status of the referral order (pending, cancelled, or completed), reminders, and/or insurance plans accepted by referral providers. Using the patient-appropriate information, the extraction component 232 is configured to generate one or more modified referral orders that are subsequently rendered by the rendering component 240 on a user interface of a computing device associated with the patient.

Figure 13:
FIG. 13 depicts an exemplary graphical user interface for presenting referral information to a patient in accordance with an embodiment of the present invention.

FIG. 13 depicts an exemplary graphical user interface (GUI) 1300 used to present patient-appropriate referral information to a patient. A patient, or a member of the patient's family, can access the GUI 1300 through a patient portal after undergoing authentication and authorization. The GUI 1300 includes a patient identification area 1312 identifying the patient. The GUI 1300 further includes a referral details tab 1314 that, when selected, presents patient-appropriate referral information in the patient-appropriate information area 1318; the patient-appropriate information includes information about the patient's pending referrals. As mentioned above, this information may include, for example, referral provider names and specialties, locations associated with providers, directions to the provider locations, reminders, priority information (urgent versus routine), ratings associated with providers, appointment times and dates, reason for referral, status of the referral order (pending, cancelled, or completed), and/or insurance plans accepted by referral providers. The patient-appropriate information area 1318 may also include an attachment area 1320. The attachment area 1320 presents selectable icons associated with patient-appropriate medical documentation such as a summarized history or a discharge summary. Additionally, the GUI 300 includes a referral history tab 1316 by which the patient can access patient-appropriate information associated with past referrals.

The GUI 1300 further includes a schedule appointment section 1324 where provider information is presented along with available appointment times (area 1328). The schedule appointment section 1324 may be presented when a referral order has been generated but has not yet been scheduled. The provider information in area 1328 may include provider names, ratings, distance from patient, contact information, and the like. Available appointment times are provided so that the patient can schedule his or her own appointment at a convenient time. The appointment times presented in the schedule appointment area 1324 are generated and presented in near real-time using, for example, cloud-based scheduling. The patient can select an appointment time (such as appointment time 1330) to immediately schedule his or her appointment. Once an appointment time has been selected, it is presented in the patient-appropriate information area 1318. The schedule appointment area 1324 also includes a search box 1326 so that the patient can search for additional providers beyond those presented in the area 1328. The additional providers may be limited to those providers who have been pre-approved by the provider or the provider's organization. Although not shown, the GUI 1300 may also include an area where the patient can submit a request to cancel a referral order. For instance, the patient may have been referred to a dermatologist for a skin rash, but the rash has since resolved, and the patient would like to cancel the appointment. Requests for cancellation may require approval by the referring provider.

The GUI 1300 further includes an action area 1322. The patient can select the checkmark in the action area 1322 for example and access one or more input fields or selectable actions. The selectable actions may include actions related to the referral order(s) such as completed or re-scheduled. Another selectable action is a pre-visit questionnaire. The patient can utilize the pre-visit questionnaire to input needed information such as demographic information, payment information, a patient-supplied medical history and review of symptoms, and a patient-supplied history of the current problem. The pre-visit questionnaire is provided to the referring provider and/or the referral provider via, for example, email, text, mail, fax, presentation on a user interface, and the like. The patient can enter feedback in the input fields. For example, the patient may indicate that he or she received outstanding care and would recommend the referral provider to others. Alternatively, the patient may indicate that waiting times were too long, the provider was unfriendly, and the like. The feedback may be communicated back to the referring provider utilizing a feedback component such as the feedback component 236 of FIG. 2. The feedback can help the referring provider evaluate his or her referral practice. The feedback may also be communicated to the referral provider for quality control purposes. The GUI 1300 may also include a reminder display area that presents reminders about upcoming appointments.

Again turning to FIG. 2, the referral service 210 further includes the scheduling component 234. The scheduling component 234 is configured to use, for example, cloud-based technology to aggregate scheduling information for a number of different providers. The scheduling component 234 presents this information in near real-time to providers and/or patients. Providers and/or patients can select from a number of available appointment times, and the scheduling component 234 makes the appointment in near real-time.

The referral service 210 also includes the feedback component 236. As mentioned above, the feedback component 236 is configured to communicate received feedback to one or more referring providers and/or referral providers. Communication may occur through, for example, email, text, mail, fax, presentation on a user interface, voicemail, and the like. The feedback component 236 is further configured to update provider ratings based on the received feedback.

The alert/notification component 238 of the referral service 210 is configured to generate alerts and/or reminders and communicate the alerts and/or reminders to providers, patients, and/or members of the patient's family. Alerts may be generated and communicated to a provider. For instance, a referral provider may be sent an alert if a high-priority referral order has been entered. Alerts may also be generated when there is a change in referral status such as "scheduled" to "patient seen," or "scheduled" to "cancelled." Additionally, alerts may be generated when additional documentation is received for a pending referral order. The alert(s) may be in the form of an email, a text message, a phone call, or a visual indicator (e.g., an exclamation point) on a user interface such as the GUI 300 of FIG. 3.

Reminders may be generated upon determining that an appointment time is scheduled in the near feature. In one aspect, reminders are sent at staggered intervals such as, for example, two weeks before, a week before, a day before, and the day of the appointment. Reminders may also be generated when a request for information has been sent by a referring provider and/or a referral provider, and the request has not been acknowledged by the receiving provider. Like alerts, reminders may be sent via email, text, voice message, or the reminders may be displayed on a user interface such as the GUI 300 of FIG. 3 or the GUI 1300 of FIG. 13. Any and all such variations are contemplated as being within the scope of the invention.

The rendering component 240 of the referral service 210 is configured to render the numerous user interfaces discussed above such as, for example, the GUIs 300, 400, 500, 600, 700, and 1300. In one aspect of the invention, the rendering component 240 is configured to render user interfaces associated with the referral service 210 as a sidebar overlaying content of a current application being utilized by a provider. Although the referral order sidebar is not integrated with the application currently being utilized by the provider, functionality associated with the referral service is still accessible to the provider.

Figure 8:
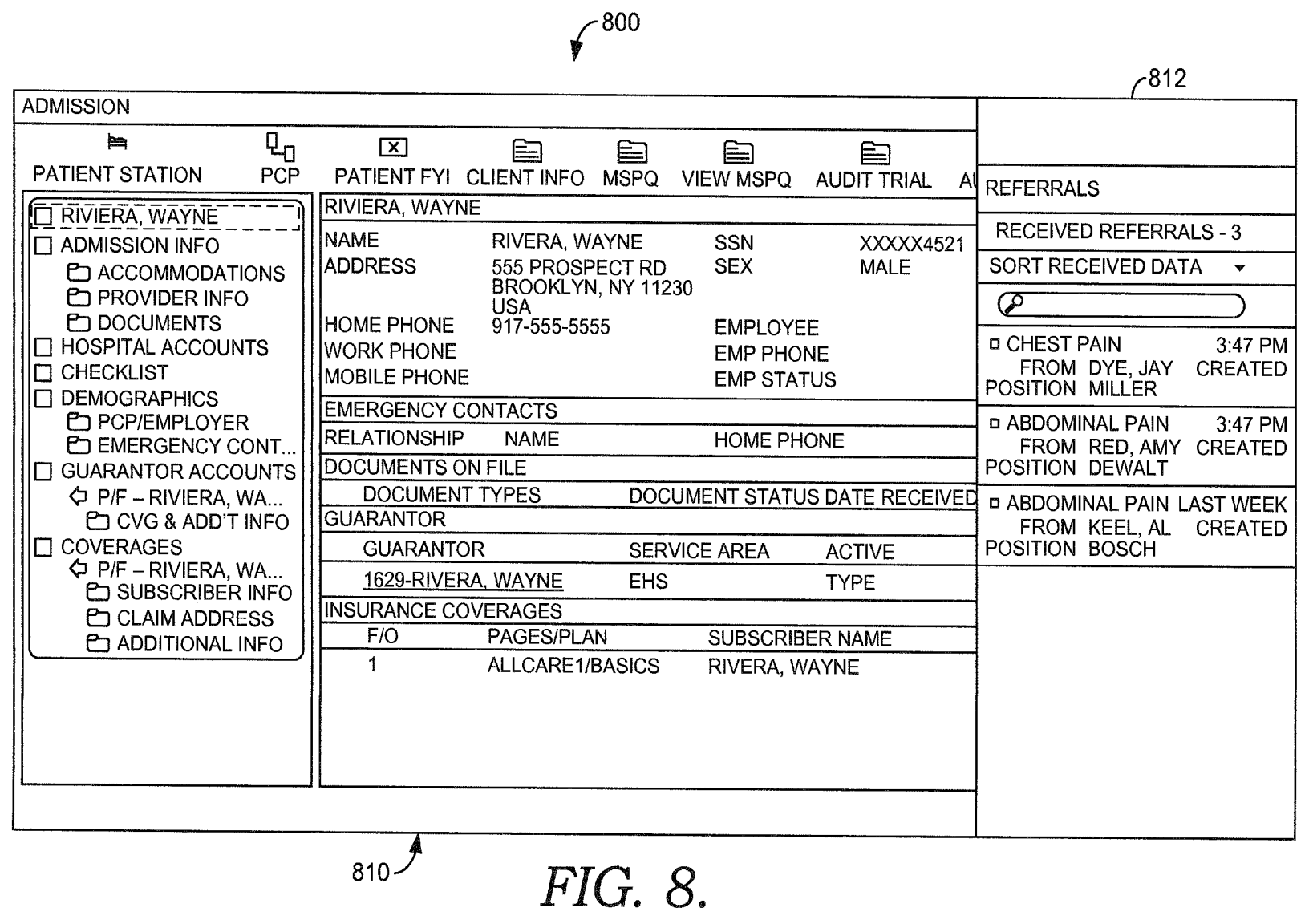

FIG. 8 depicts this aspect of the invention. FIG. 8 depicts a user interface (UI) 800 having an active application window 810 and a referral sidebar 812. This is useful when the provider wants to initiate functionality associated with the referral service while still working within the context of the application window 810. The referral sidebar 812 would be instantiated upon the provider signing in and being authenticated.

FIG. 9 depicts a flow diagram illustrating an exemplary method 900 of generating a unified patient referral worklist for a provider. At a step 910, a first referral order associated with a first patient is received from a first medical organization. The first referral order may be stored in an electronic medical record system associated with the organization and may have been created by a provider associated with the first medical organization.

At a step 912, a second referral order associated with a second patient is received from a second medical organization. The second referral order may be stored in an electronic medical record system associated with the second medical organization and may have been created by a provider associated with the second medical organization. The second medical organization may be different from the first medical organization. Further, the two medical organizations may maintain disparate electronic health record systems thus preventing interoperability with each other. As well, the second patient may be different from the first patient.

At a step 914, a provider associated with the first referral order and the second referral order is determined. The provider may be associated with the first referral order and the second referral order if the provider is identified as either a referral provider or a referring provider on the referral orders. This determination may be made by a determining component of a referral service such as the determining component 226 of FIG. 2.

At a step 916, a unified patient referral worklist is generated using the first and second referral orders. The unified patient referral worklist is specific to the provider and/or the provider's office, and it includes all incoming and outgoing referral orders for that provider. At a step 918, the unified patient referral worklist is presented on a user interface of a computing device associated with the provider and/or the provider's office. The unified patient referral worklist is filterable and sortable. Individual referral orders can be selected to view details associated with the referral order. The details may include an in-depth note addressing the reason for the referral as well as medical documentation that helps the referral provider to better understand the patient and the patient's health problems.

Turning to FIG. 10, a flow diagram is depicted illustrating an exemplary method 1000 of generating a patient-centric referral order in a healthcare setting. At a step 1010, a first referral order is received for a patient. The first referral order may be received by a receiving component of a referral service such as the receiving component 224 of FIG. 2. The first referral order may have been created by a referring provider associated with a healthcare facility and may refer the patient to a referral provider in order to address a health concern of the patient.

At a step 1012, a second referral order is received for the patient. The second referral order may have been created by the same referring provider who created the first referral order, or, alternatively, the second referral order may have been created by a different referring provider. As well, the second referral order may have been received from a different medical organization than the first referral order; the different medical organizations may maintain disparate electronic medical record systems.

At a step 1014, an instance of commonality between the first and second referral orders is determined by, for example, a patient-centric referral component such as the patient-centric referral component 228 of FIG. 2. For instance, medical specialties of each referral order may be determined, and a common location may be identified that includes providers who practice the determined specialties. By way of illustrative example, a first referral order for Patient X may be for an evaluation of a heart murmur. The referring provider may specify that the patient should see a cardiologist. Alternatively, if the referring provider does not specify the medical specialty, the patient-centric referral component may determine that a cardiologist would be best-suited to evaluate the heart murmur. A second referral order for Patient X may be for an evaluation of a hernia. Again, the referring provider may specify that the patient should see a surgeon, or the patient-centric referral component may make this determination if the referring provider does not specify the medical specialty. A common location that includes both a cardiologist and a surgeon is then determined. The common location may be a physical building that houses a cardiology group and a surgeon group; the cardiology group and the surgeon group may have separate practices even though they are located in the same building. The common location may also include a multi-practice provider group that includes providers that practice both of these specialties.

At a step 1014, a third referral order is generated based on the instance of commonality between the first and second referral order. Using the example set forth above, a third referral order for Patient X includes the referral order for the heart murmur and the referral order for the hernia. The third referral order also includes the common location information. The third referral order may subsequently be presented on a user interface of a computing device associated with the provider and/or the patient.

Figure 11:
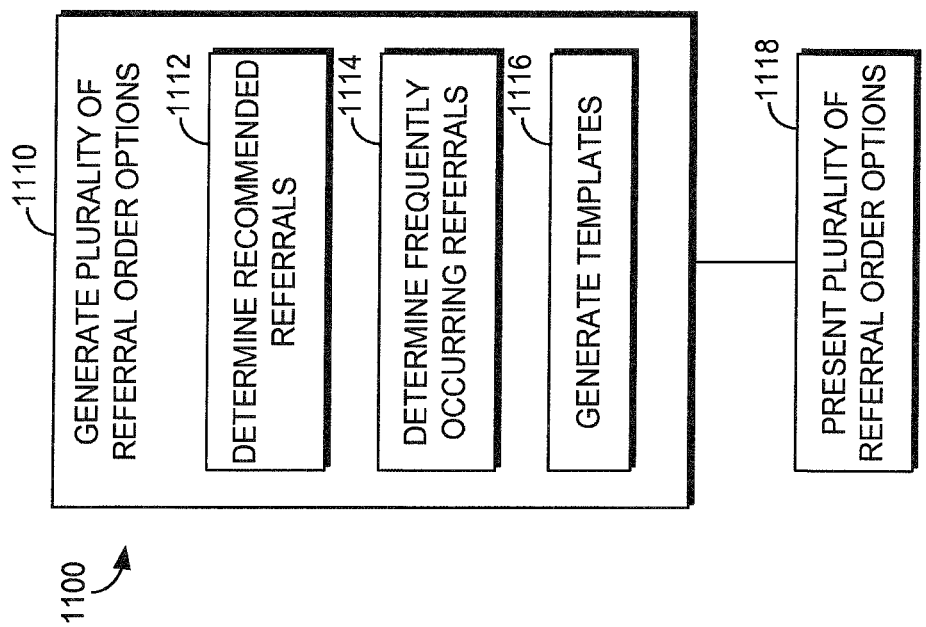
FIG. 11 is a flow diagram that illustrates an exemplary method of generating a plurality of referral order options in accordance with an embodiment of the present invention.

FIG. 11 depicts a flow diagram of an exemplary method 1100 of generating and presenting to a provider a plurality of referral order options for a patient. At a step 1110, the plurality of referral order options is generated. This may be done by, for example, a referral order option component such as the referral order option component 230 of FIG. 2. The plurality of options is generated by determining recommended referral options based at least in part on the patient's medical history and medical standards of care (this is shown at a step 1112). The patient's medical history (stored in association with the patient's electronic medical record) gives an indication of the types of tests and procedures, including screening tests and procedures that the patient has undergone. The medical history may also indicate if the patient is at a higher than normal risk of developing a certain disease or condition. This information is evaluated in the context of medical standards of care to determine if the patient should be referred for evaluation. The medical standards of care may be specific to a provider, a healthcare facility that is caring for the patient, or the medical standards of care may be promulgated by national or state governing bodies or organizations.

At a step 1114, frequently occurring referrals for the provider are determined. This may be done by analyzing referral patterns of the referring provider while taking into account the patient's medical history. Referral patterns may include frequently occurring: 1) reasons for referrals; 2) providers referred to; 3) medical specialties referred to; and 4) locations referred to. The provider's referral patterns are analyzed in the context of the patient's medical history. For instance, the referring provider may frequently refer to a certain endocrinologist for diabetes evaluations. However, the patient's medical history indicates that the patient does not have diabetes nor is the patient at risk for developing diabetes. Based on this, the referral order for the endocrinologist would not be presented.

At a step 1116, one or more templates are generated that can be used by the provider to generate customized referral orders. The one or more templates may also include templates that have been generated by a medical facility affiliated with the provider. At a step 1118, the recommended referral order options, the frequently referred options, and the templates are presented on a user interface of a computing device associated with the provider and/or the provider's office.

The referring provider is able to select one or more of the plurality of referral order options on the user interface. Upon selection, the provider is presented with a detail screen. The detail screen may be pre-populated with information such as name of patient, type of consult, priority, provider name, specialty, and the like. The provider can input a detailed reason for referral and a medical note outlining general information about the patient. The referring provider can also attach any pertinent medical documentation (labs, images, etc.) that may help the referral provider evaluate the patient. The medical note and the attached documentation may be persisted to other referral orders being created by the referring provider, thus eliminating the need for the referring provider to input the information each time a referral order is created. Once the details have been inputted by the referring provider, the referral order is generated.

Figure 12:
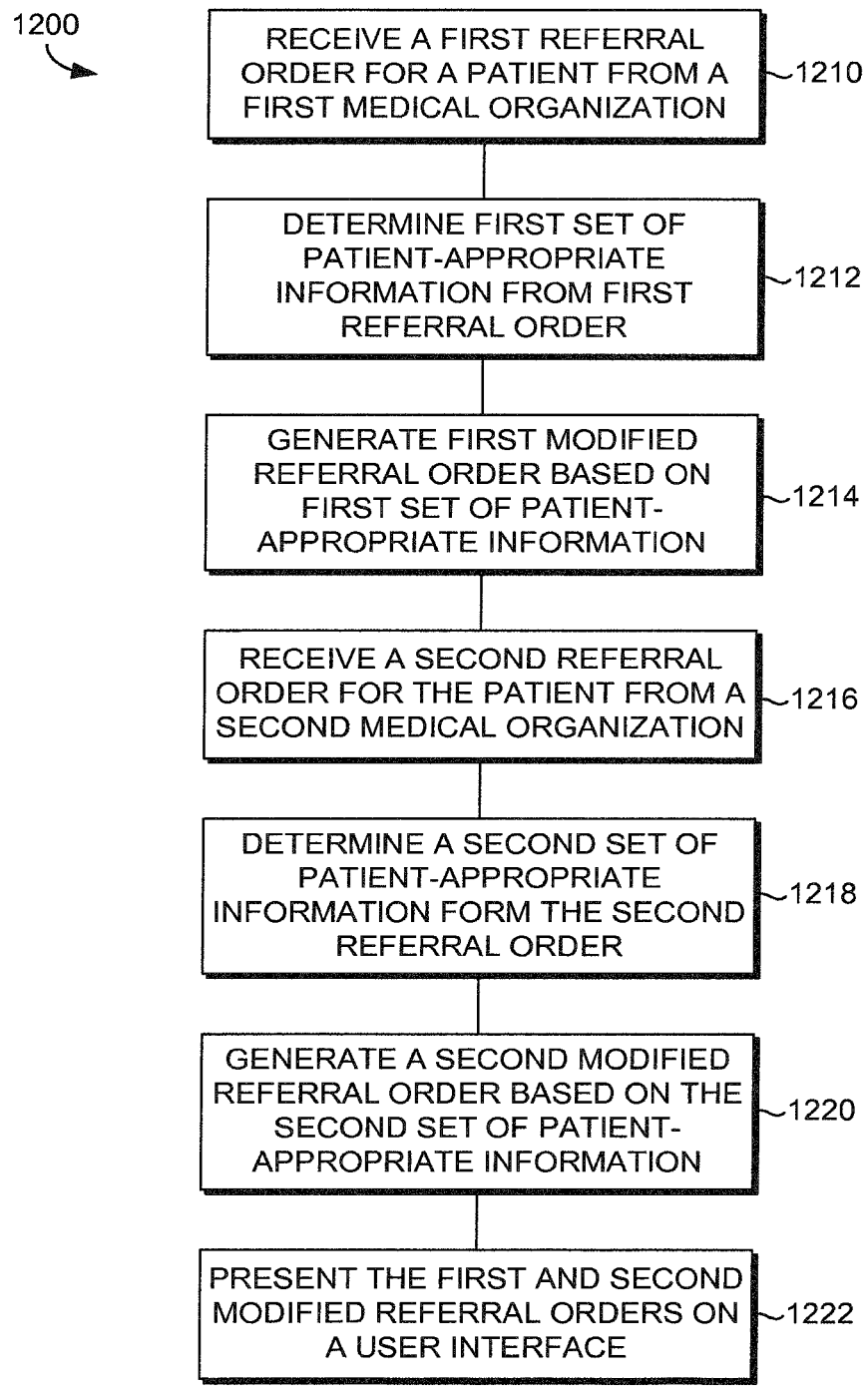
FIG. 12 is a flow diagram that illustrates an exemplary method of generating and presenting patient-appropriate referral information in accordance with an embodiment of the present invention.

Turning to FIG. 12, a flow diagram is depicted illustrating a method 1200 of generating and presenting patient-appropriate referral information. At a step 1210, a first referral order for a patient is received from a first medical organization. The first referral order may be received by a receiving component such as the receiving component 224 of FIG. 2. The first referral order may be stored in an EMR associated with the first medical organization.

At a step 1212, a first set of patient-appropriate information is determined from the first referral order. The first referral order may contain information that is important and relevant to a referring provider and/or a referral provider, but this information may not be particularly relevant to the patient. For instance, the referral order may contain technical terms, lab or procedure results, insurance authorization codes, and the like that may be relevant to a provider but not to the patient. An extraction component such as the extraction component 232 of FIG. 2 identifies and extracts the patient-appropriate information. Information that may be appropriate to the patient may include, for example, a brief reason for referral, provider information, a priority of the referral, location information, directions, ratings of different providers, scheduled appointment times and dates, available appointment times and dates if the referral has not been scheduled, and the like.

At a step 1214, a first modified referral order is generated using the patient-appropriate information. At a step 1216, a second referral order for the patient is received from a second medical organization. The second medical organization may be different from the first medical organization. Further, the second medical organization may have an electronic medical record system that is different from the first medical organization; the disparate systems may limit interoperability with each other. At a step 1218, a second set of patient-appropriate information is determined from the second referral order. Like above, this information is relevant to the patient. At a step 1220, a second modified referral order is generated using the second set of patient-appropriate information.

At a step 1222, the first and second modified referral orders are presented on a user interface of a computing device associated with the patient. The patient is able to interact with the modified referral orders. For instance, the patient can indicate if he or she completed the appointment. Further, the patient can provide feedback regarding the quality of care received from the referral provider; the feedback may be communicated to both the referring provider and the referring provider. The patient may also reschedule an appointment with a provider by selecting from available appointment times for the provider. The patient may also receive appointment reminders.

In conclusion, the present invention enables both patients and providers to manage referral orders in a unique way. Providers can improve their referral practice by better managing their incoming and outgoing referrals, generating referral orders that include substantive information that improves quality of care, receiving feedback from patients, and generating patient-centric referral orders. Patients can have an improved healthcare experience. For example, patients can view pending referrals and receive reminders which may improve patient compliance. As well, patient-centric referral orders make it less burdensome for patients who have multiple referral orders directed to different providers in different locations. Patients can also schedule or reschedule appointments in near real-time without having to navigate the maze of a provider's telephone directory system.

The present invention has been described in relation to particular embodiments, which are intended in all respects to be illustrative rather than restrictive. Further, the present invention is not limited to these embodiments, but variations and modifications may be made without departing from the scope of the present invention.

What is claimed is:

1. One or more non-transitory computer-readable storage media having embodied thereon computer-executable instructions that, when executed by a server, perform a method of generating patient-appropriate referral orders on a graphical user interface associated with a patient portal, the method comprising:

receiving, at a referral service including a processor and a memory in a computer system, a referral order from a first computing device associated with a medical organization, the referral order being for a patient and including referral information;

identifying, at a referral service, a first portion of referral information and a second portion of referral information from the referral order, the first portion comprising one or more of the healthcare provider's note providing a detailed reason for referral and a medical note outlining general information about the patient including at least a past medical history and a social history, and the second portion of referral information comprising patient-appropriate referral information comprising one or more of a referring provider name, a referral provider name, a reason for the referral, and an appointment date and time;

generating a modified referral order by extracting, at the referral service, the second portion of referral information from the referral order;

utilizing the modified referral order comprising the extracted second portion of referral information, generating, at the referral service, a patient-centric referral order interface corresponding to the referral order, the patient-centric referral order interface including the extracted second portion of referral information from the referral order, one or more selectable action icons, and an option to search for additional referral providers, wherein one or more actions related to the referral order are initiated upon receiving selection of one or more of the one or more selectable action icons and the one or more actions include actions that change a status of the referral order, wherein the one or more selectable action icons are based on the status of the referral order at the referral service, and wherein the patient-centric referral order interface excluding the first portion of referral information;

presenting, by the referral service, the patient-centric referral order interface including the one or more selectable action icons for display on the graphical user interface within the patient portal accessible from a second computing device associated with the patient, wherein the patient portal allows the second computing device associated with the patient to communicate with the referral service to manage referral orders via the graphical user interface using a web browser; and upon receiving selection of at least one of the selectable action icons, the referral service initiating the selected action, changing the status of the referral order, generating an alert indicating the change in the status of the referral order, and modifying the patient-centric referral order interface to display on the graphical user interface information related to the selected action in real-time simultaneously with the second portion of referral information, a status of the referral order, a referral type, a priority level, and the alert.

2. The computer-readable media of claim 1, wherein the method further comprises upon determining a referral appointment associated with the referral order has not been scheduled, modifying the patient-centric referral order interface to display, simultaneously with the second portion of referral information, one or more available appointment times for the referral order.

3. The computer-readable media of claim 2, wherein a selectable option to schedule an appointment is provided for simultaneous display with the one or more available appointment times for the referral order.

4. The computer-readable media of claim 1, wherein the patient-centric referral order interface includes one or more additional providers for the referral order provided for display simultaneous with the second portion of referral information, the one or more additional providers being pre-approved by the referring provider.

5. The computer-readable media of claim 1, wherein the referral order comprises an indication of a temporary or permanent transfer of care for the patient from a referring provider to a referral provider.

6. The computer-readable media of claim 1, further comprising:
receiving patient feedback regarding the referral order via an input field within the patient-centric referral order interface, the feedback comprising the patient's evaluation of a quality of care received from a referral provider associated with the referral order; and
communicating the patient feedback to a referring provider associated with the referral order.

7. A computerized method for generating patient-appropriate referral orders on a graphical user interface associated with a patient portal, the method comprising:
receiving, at a referral service including a processor and a memory in a computer system, a referral order from a first computing device associated with a medical organization, the referral order being for a patient and including referral information;
identifying, at the referral service, a first portion of referral information and a second portion of referral information from the referral order, the first portion comprising one or more of the healthcare provider's note providing a detailed reason for referral and a medical note outlining general information about the patient including at least a past medical history and a social history, and the second portion of referral information comprising patient-appropriate referral information comprising one or more of a referring provider name, a referral provider name, a reason for the referral, and an appointment date and time;
generating a modified referral order by extracting, at the referral service, the second portion of referral information from the referral order;

utilizing modified referral order comprising the extracted second portion of referral information, generating, at the referral service, a patient-centric referral order interface corresponding to the referral order, the patient-centric referral order interface including the second portion of referral information from the referral order, one or more selectable action icons, and an option to search for additional referral providers, wherein one or more actions related to the referral order are initiated upon receiving selection of one or more of the one or more selectable action icons and the one or more actions include actions that change a status of the referral order, wherein the one or more selectable action icons are based on the status of the referral order at the referral service, and wherein the patient-centric referral order interface excluding the first portion of referral information;

presenting, by the referral service, the patient-centric referral order interface including the one or more selectable action icons for display on the graphical user interface within the patient portal accessible from a second computing device associated with the patient, wherein the patient portal allows the second computing device associated with the patient to communicate with the referral service to manage referral orders via the graphical user interface using a web browser; and upon receiving selection of at least one of the selectable action icons, the referral service initiating the selected action, changing the status of the referral order, generating an alert indicating the change in the status of the referral order, and modifying the patient-centric referral order interface to display on the graphical user interface information related to the selected action in real-time simultaneously with the second portion of referral information, a status of the referral order, a referral type, a priority level, and the alert.

8. The computerized method of claim 7, wherein the method further comprises upon determining a referral appointment associated with the referral order has not been scheduled, modifying the patient-centric referral order interface to display, simultaneously with the second portion of referral information, one or more available appointment times for the referral order.

9. The computerized method of claim 8, wherein a selectable option to schedule an appointment is provided for simultaneous display with the one or more available appointment times for the referral order.

10. The computerized method of claim 7, wherein the patient-centric referral order interface includes one or more additional providers for the referral order provided for display simultaneous with the second portion of referral information, the one or more additional providers being pre-approved by the referring provider.

11. The computerized method of claim 7, wherein the referral order comprises an indication of a temporary or permanent transfer of care for the patient from a referring provider to a referral provider.

12. The computerized method of claim 7, further comprising:
receiving patient feedback regarding the referral order via an input field within the patient-centric referral order interface, the feedback comprising the patient's evaluation of a quality of care received from a referral provider associated with the referral order; and
communicating the patient feedback to a referring provider associated with the referral order.

13. The computerized method of claim 7, further comprising: receiving a plurality of additional referral orders for the patient, each additional referral order comprising a first portion of referral information and a second portion of referral information, the first portion comprising one or more of the healthcare provider's note providing a detailed reason for referral and a medical note outlining general information about the patient including at least a past medical history and a social history, and the second portion of referral information comprising patient-appropriate referral information comprising one or more of a referring provider name, a referral provider name, a reason for the referral, and an appointment date and time.

14. The computerized method of claim 13, wherein the patient-centric referral order interface generated further corresponds to the plurality of additional referral orders and further includes the second portion of referral information from each of the additional referral orders, the patient-centric referral order interface excluding the first portion of referral information form the additional referral orders.

15. A system at a referral service for generating patient-appropriate referral orders on a graphical user interface associated with a patient portal, the system comprising:
one or more processors; and
one or more computer storage media storing computer-usable instructions to cause the one or more processors to perform operations to:
receive, at the referral service, a first referral order from a first computing device associated with a medical organization, the first referral order being for a patient and including a first set of referral information;
identify, at the referral service, a first portion of referral information and a second portion of referral information from the first set of referral information, the first portion comprising one or more of the healthcare provider's note providing a detailed reason for referral and a medical note outlining general information about the patient including at least a past medical history and a social history, and the second portion of referral information comprising patient-appropriate referral information comprising one or more of a referring provider name, a referral provider name, a reason for the referral, and an appointment date and time;
receive, at the referral service, a second referral order from a second computing device associated with a second medical organization, the second referral order being for the patient and including a second set of referral information;
identify, by the referral service, a third portion of referral information and a fourth portion of referral information from the second set of referral information, the third portion comprising one or more of the healthcare provider's note providing a detailed reason for referral and a medical note outlining general information about the patient including at least a past medical history and a social history, and the fourth portion of referral information comprising patient-appropriate referral information comprising one or more of a referring provider name, a referral provider name, a reason for the referral, and an appointment date and time;
extract, at the referral service, the second portion of referral information from the first set of referral information and the fourth portion of referral information from the second set of referral information;
utilizing the extracted second portion from the first set of referral information and the extracted fourth portion from the second set of referral information, generate, at the referral service, a patient-centric referral order interface corresponding to the first referral order and the second referral order, the patient-centric referral order interface including a first modified referral order that includes the second portion from the first set of referral information and a second modified referral order that includes the fourth portion from the second set of referral information, the patient-centric referral order interface further comprising one or more selectable action icons and an option to search for additional referral providers, wherein one or more actions related to one or more of the first referral order and the second referral order are initiated upon receiving selection of one or more of the one or more selectable action icons and the one or more actions include actions that change a status of the referral order, wherein the one or more selectable action icons are based on the status of the first referral order and the second referral order at the referral service, and wherein and excluding the first portion of the first set of referral information and the third portion of the second set of referral information are excluded;
present, by the referral service, the patient-centric referral order interface including the one or more selectable action icons for display on the graphical user interface within a patient portal accessible from a third computing device associated with the patient, wherein the patient portal allows the second computing device associated with the patient to communicate with the referral service to manage referral orders via the graphical user interface using a web browser; and
upon receiving selection of at least one of the selectable action icons, the referral service initiating the selected action, changing the status of the referral order, generating an alert indicating the change in the status of the referral order, and modifying the patient-centric referral order interface to display on the graphical user interface information related to the selected action in real-time simultaneously with first modified referral order and the second modified referral order, a status of the referral order, a referral type, a priority level, and the alert.

16. The system of claim 15, wherein the operations further comprise upon determining a referral appointment associated with at least one of the first referral order and the second referral order has not been scheduled, modify the patient-centric referral order interface to display, simultaneously with the second portion and fourth portion of referral information, one or more available appointment times for the at least one of the first referral order and the second referral order.

17. The system of claim 16, wherein a selectable option to schedule an appointment is provided for simultaneous display with the one or more available appointment times.

18. The system of claim 15, wherein the patient-centric referral order interface includes one or more additional providers for the first referral order and the second referral order provided for display simultaneous with the second portion and the fourth portion of referral information.

19. The system of claim 15, wherein the first referral order and the second referral order each comprises an indication of a temporary or permanent transfer of care for the patient from a referring provider to a referral provider.

20. The system of claim 15, wherein the operations further comprise:
- receive patient feedback regarding at least the first referral order via an input field within the patient-centric referral order interface, the feedback comprising the patient's evaluation of a quality of care received from a referral provider associated with the first referral order; and
- communicate the patient feedback to a referring provider associated with the first referral order.

\* \* \* \* \*